United States Patent
McFall et al.

[11] Patent Number: 5,827,258
[45] Date of Patent: Oct. 27, 1998

[54] ADJUSTABLE COMPOUND SANITARY NAPKIN

[75] Inventors: Ronald Ray McFall, West Chester; Nicholas Albert Ahr; Letha Margory Hines, both of Cincinnati, all of Ohio

[73] Assignee: The Procter & Gamble Company, Cincinnati, Ohio

[21] Appl. No.: 900,252

[22] Filed: Jul. 25, 1997

[51] Int. Cl.$^6$ .................................................. A61F 13/15
[52] U.S. Cl. ...................... 604/385.1; 604/378; 604/386
[58] Field of Search .................. 604/358, 378, 604/385.1, 385.2, 386, 387

[56] References Cited

U.S. PATENT DOCUMENTS

| | | | |
|---|---|---|---|
| H1634 | 2/1997 | Oetjen et al. | 604/385.1 |
| 2,295,016 | 9/1942 | Scribner . | |
| 2,331,355 | 10/1943 | Strongson . | |
| 2,662,527 | 12/1953 | Jacks . | |
| 2,683,457 | 7/1954 | Cunningham . | |
| 2,929,379 | 3/1960 | Poulsen . | |
| 2,965,102 | 12/1960 | Harwood . | |
| 3,183,909 | 5/1965 | Roehr . | |
| 3,406,689 | 10/1968 | Hicks et al. . | |
| 3,512,530 | 5/1970 | Jones . | |
| 3,528,422 | 9/1970 | Hodas . | |
| 3,570,492 | 3/1971 | Bettencourt . | |
| 4,046,147 | 9/1977 | Berg . | |
| 4,397,644 | 8/1983 | Matthews et al. | 604/378 |
| 4,425,130 | 1/1984 | DesMarais | 604/389 |
| 4,596,570 | 6/1986 | Jackson et al. | 604/387 |
| 4,631,062 | 12/1986 | Lassen et al. . | |
| 4,798,603 | 1/1989 | Meyer et al. | 604/378 |
| 4,804,380 | 2/1989 | Lassen et al. | 604/385.1 |
| 4,908,026 | 3/1990 | Sukiennik et al. | 604/378 |
| 4,938,756 | 7/1990 | Salek | 604/368 |
| 5,007,906 | 4/1991 | Osborn et al. | 604/385.1 |
| 5,057,096 | 10/1991 | Faglione | 604/385 |
| 5,264,268 | 11/1993 | Luceri et al. | 428/138 |
| 5,391,160 | 2/1995 | Runeman et al. | 604/378 |
| 5,462,537 | 10/1995 | Carr et al. | 604/368 |
| 5,507,735 | 4/1996 | Van Iten et al. | 604/385.1 |
| 5,599,337 | 2/1997 | McCoy | 604/385.1 |
| 5,669,898 | 9/1997 | Ahr | 604/387 |
| 5,733,274 | 3/1998 | Osborn | 604/385.1 |

FOREIGN PATENT DOCUMENTS

| | | |
|---|---|---|
| 0 426 197 A2 | 5/1991 | European Pat. Off. . |
| 05-115506 | 5/1993 | Japan . |
| 1 295 493 | 11/1972 | United Kingdom . |
| 2 232 600 | 12/1990 | United Kingdom . |
| WO 94/16658 | 8/1994 | WIPO . |
| WO 95/16422 | 6/1995 | WIPO . |

*Primary Examiner*—Mark O. Polutta
*Attorney, Agent, or Firm*—Edward J. Milbrada; Jeffrey V. Bamber; Steven W. Miller

[57] ABSTRACT

The present invention pertains to a compound sanitary napkin. The compound sanitary napkin comprises an acquisition/storage member including an absorbent element and an outer cover. The acquisition/storage member preferably has a base and an apex; the apex being vertically opposed to the base. The width of the base is greater than the width of the apex. The compound sanitary napkin further comprises an accumulation member that is connected to the acquisition/storage member juxtaposed the base. The accumulation member comprises a liquid impervious backsheet and an absorbent material joined thereto. Preferably, the accumulation member includes a backsheet, a topsheet joined to the backsheet and an absorbent core disposed between the backsheet and the topsheet. The compound sanitary napkin of the present invention further comprises a bearing member which connects the acquisition/storage member to the accumulation member; the acquisition/storage member being slidably connected to the bearing member and the bearing member being joined to the accumulation member adjacent their respective end edges. In an alternative embodiment, the bearing member can flare to a greater width adjacent the end edges of the accumulation member.

14 Claims, 3 Drawing Sheets

ADJUSTABLE COMPOUND SANITARY NAPKIN

FIELD OF THE INVENTION

The present invention relates to disposable sanitary napkins. As used herein, sanitary napkins are considered to be absorbent devices designed to be worn externally of the body by women, usually during their menstrual periods, and to receive and contain menses and other bodily discharges. Disposable sanitary napkins are intended to be discarded after use and soiling rather than being cleaned and reused.

BACKGROUND OF THE INVENTION

In their simplest form, disposable sanitary napkins comprise an absorbent element (sometimes referred to as an absorbent core) interposed between a liquid pervious body-contacting element (sometimes referred to as a topsheet or an overwrap) and a liquid impervious protective barrier (sometimes referred to as a backsheet). The absorbent element is intended to receive and contain menses and other vaginal discharges. The body-contacting element is intended to provide more or less comfortable and dry-feeling contact with body surfaces while allowing free passage of fluids therethrough into the absorbent element. The protective barrier is intended to prevent menses or other bodily fluids which are expelled or which escape from the absorbent element from soiling the wearer's garments.

In addition to the three functional elements mentioned above, disposable sanitary napkins are generally provided with means for supporting the device adjacent the wearer's crotch area, even as the wearer moves, where it can most effectively perform its intended function. Typically, sanitary napkins are provided with an adhesive attachment means for securing the device to the inner crotch area of the wearer's undergarments.

While previously known sanitary napkins do perform their intended function, each conventional design suffers from certain deficiencies in one or more of absorbency of body fluids, protection of the wearer's garments from soiling, and/or physical comfort to the wearer.

With respect to disposable sanitary napkins, at least two general classes presently exist. One such class is identified as being intended for the absorption of medium to high menstrual flows. These sanitary napkins offer a relatively high absorptive capacity. Absorptive capacity is commonly achieved by providing the sanitary napkin with a relatively thick and bulky absorbent member. While having a relatively high absorptive capacity, the bulkiness of the absorbent member may cause a certain degree of wearing discomfort.

A second class of sanitary napkins are intended for light or low menstrual flows and are commonly referred to as pantiliners or pantishields. Sanitary napkins of this class, as a group, are thinner, somewhat more flexible and generally more comfortable than those of the first class. However, sanitary napkins of the second class typically lack the absorptive capacity of sanitary napkins of the first class.

One attempt to provide the benefits of the previously described two classes of sanitary napkins into a single compound sanitary napkin is disclosed in commonly assigned U.S. Pat. No. 4,425,130 issued to DesMarais on Jan. 10, 1984. The compound sanitary napkin of DesMarais comprises a primary menstrual pad and a panty protector joined to one another at their corresponding ends in such a manner that the two components are free to move relative to one another along essentially their entire common length. The primary menstrual pad is intended to absorb the bulk of the bodily fluids discharged by the wearer, while the panty protector is intended to protect the wearer's garments from soiling. In use, the relative freedom of movement between the primary menstrual pad and the panty protector serves to maintain the primary menstrual pad adjacent the wearer's crotch region while the panty protector remains associated with the wearer's undergarment. While the relative freedom of movement between the primary menstrual pad and the panty protector serves to maintain the primary menstrual pad near the wearer's crotch region, this freedom of movement may lead to a lack of stability if the primary menstrual pad moves laterally beyond the side edges of the panty protector, providing an opportunity for soiling the wearer's undergarment. Furthermore, the relative freedom of movement between the primary menstrual pad and the panty protector alone may be insufficient to capture bodily fluid as it exits the wearer's vaginal opening.

U.S. Statutory Invention Registration H1614, published on Nov. 5, 1996 in the name of Mayer, et al. describes a compound sanitary napkin comprising a primary absorbent member and a secondary absorbent member having a common length. The primary absorbent member, which is intended to absorb the bulk of bodily fluids received by the compound sanitary napkin, comprises an absorbent core and a fluid pervious topsheet superposed on the absorbent core. The secondary absorbent member comprises a fluid pervious topsheet, a fluid impervious backsheet joined to the topsheet and an absorbent element positioned between the topsheet and the backsheet. The primary absorbent member and the secondary absorbent member have a common length and the primary absorbent member is affixed to the secondary absorbent member by union means in such a manner that the longest unattached distance between adjacent points of attachment is less than 75% of the common length. While such compound sanitary napkins provide improved absorbency and protection, the fit of such sanitary napkins cannot be tailored to match the particular needs of an individual wearer.

Thus, it is an object of the present invention to provide a sanitary napkin with improved contact with a wearer's pudendal region. It is a further object of the present invention to provide a sanitary napkin that maintains such contact throughout a wide range of wearer movements and levels of activity. It is still a further object of the present invention to provide a sanitary napkin that makes effective use of the full absorbent capacity available in the structure.

SUMMARY OF THE INVENTION

The present invention is a compound sanitary napkin comprising an adjustable acquisition/storage member and an accumulation member. The present invention provides for protection of a wearer's garments from soiling and for physical comfort to the wearer because the acquisition/storage member can be adjusted to match an individual wearer's needs for both protection and comfort. The acquisition/storage member intercepts bodily fluids, such as menses, as they are first exuded and comprises an absorbent element and an outer cover. In a preferred embodiment, the acquisition/storage member has a base and an apex; the apex being vertically opposed to the base. The width of the base is greater than the width of the apex (i. e. the acquisition/storage member has a rounded triangular cross section). Preferably, the acquisition/storage member comprises an absorbent element and an outer cover. In a particularly preferred embodiment, the absorbent element comprises a web of material which is folded to form a pair of walls having two plies except adjacent the longitudinal centerline whereby the lateral separation of the fold lines forming the walls defines the lateral width of the base. The absorbent element is also stiffer in the wall portions thereof than adjacent the longitudinal centerline because the walls thereof comprise two plies of material. The outer cover wraps the absorbent element and the bearing member (discussed below). The compound sanitary napkin further comprises a accumulation member. The accumulation member preferably comprises a liquid impervious backsheet and an absorbent material joined thereto. Optimally, the accumulation member comprises a backsheet, a topsheet joined to the backsheet and an absorbent core disposed between the backsheet and the topsheet. A bearing member carries the acquisition/storage member and allows longitudinal positioning thereof. In a preferred embodiment, the bearing member is joined to the accumulation member adjacent the end edges thereof. Particularly preferably, the acquisition/storage member has a longitudinal length that is shorter than the longitudinal length of the central region of the compound sanitary napkin of the present invention. In alternative embodiments the acquisition/storage member can have cross sections other than rounded triangular and the bearing member can flare from the an end of the acquisition/storage member to an end of the accumulation member.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and wherein:

DETAILED DESCRIPTION OF THE INVENTION

General Description of the Present Invention

This invention is of a compound sanitary napkin having an adjustable acquisition/storage member. The present invention provides for protection of a wearer's garments from soiling and for physical comfort to the wearer because the acquisition/storage member can be adjusted to match an individual wearer's needs for both protection and comfort. The term "sanitary napkin", as used herein, refers to an article which is worn by females adjacent to the pudendal region and which is intended to absorb and contain the various exudates which are discharged from the body (e.g., blood, menses, and urine) and which is intended to be discarded after a single use (i.e., it is not intended to be laundered or otherwise restored or reused). The term "compound sanitary napkin", as used herein, refers to a sanitary napkin comprised of separate components joined to one another to form a unitary structure. Interlabial devices which reside at least partially within a wearer's interlabial space are also within the scope of this invention. As used herein, the term "pudendal" refers to the externally visible female genitalia and is limited to the labia majora, the labia minora, the clitoris, the vaginal introitus, and the vestibule.

Figure 1:
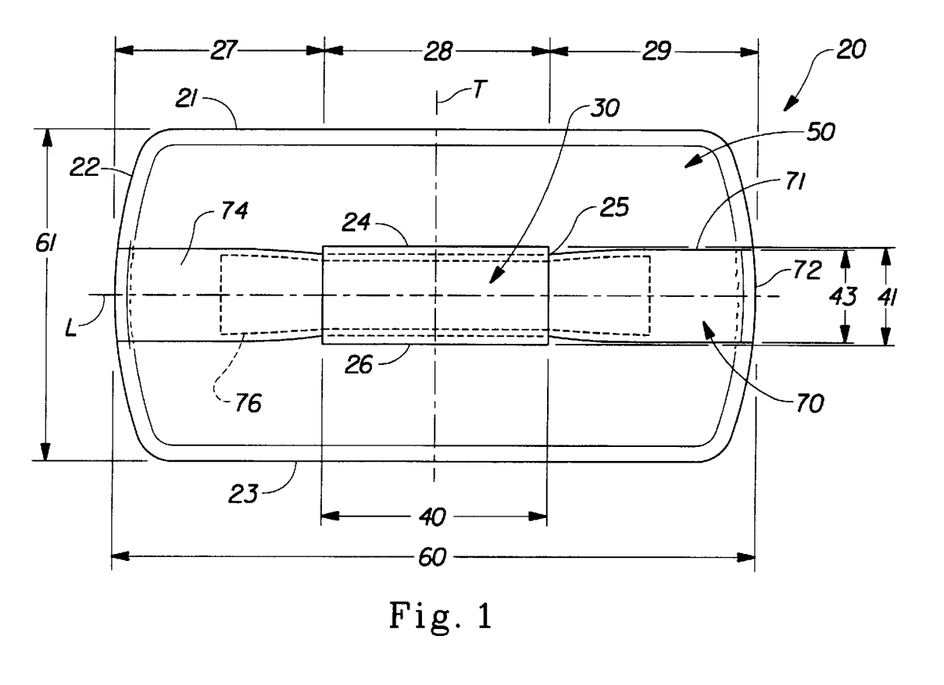
FIG. 1 is a top plan view of a preferred embodiment of the compound sanitary napkin of the present invention.
Figure 2:
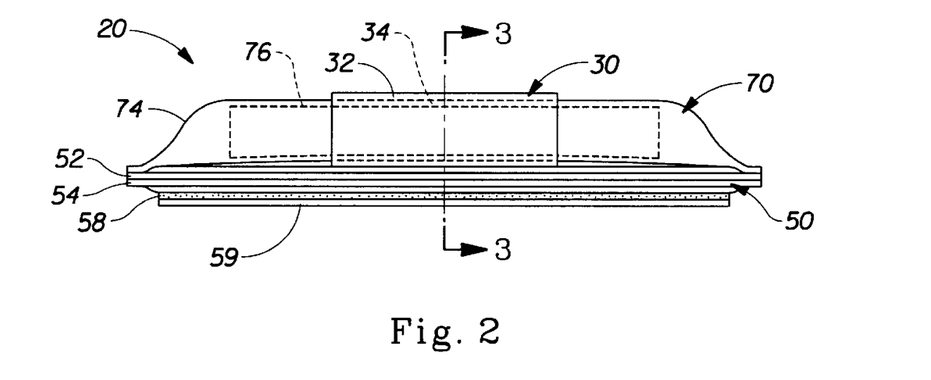
FIG. 2 is a side elevation view of the compound sanitary napkin shown in FIG. 1.
Figure 3:
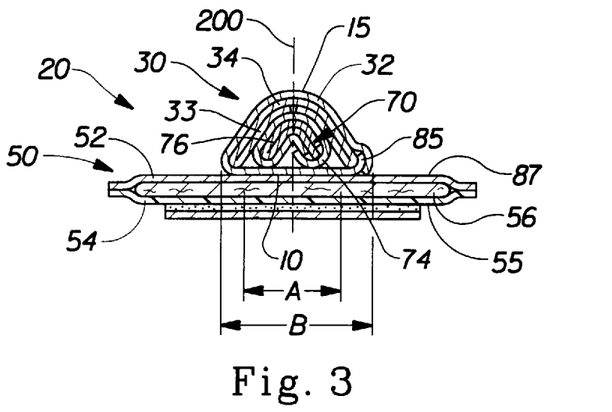
FIG. 3 is cross-sectional views of the compound sanitary napkin shown in FIGS. 1 and 2 as taken along section line 3—3 of FIG. 2.

FIGS. 1–3 show one preferred embodiment of a compound sanitary napkin 20 of the present invention. As can be seen in FIGS. 1–3, the compound sanitary napkin 20 comprises an acquisition/storage member 30 and a accumulation member 50 connected by bearing member 70. The acquisition/storage member 30 and the accumulation member 50 are connected because the acquisition/storage member is slidably attached to the bearing member 70 and the bearing member 70 is joined to the accumulation member 50 (As used herein, the term "joined" encompasses configurations whereby an element is directly secured to another element by affixing the element to the other element, as well as configurations whereby an element is indirectly secured to another element by affixing the element to an intermediate member or members which in turn are affixed to the other element.). The compound sanitary napkin has two surfaces, a body contacting or facing surface 87, and a garment facing or contacting surface 55. The acquisition/storage and accumulation members 30, 50 each have corresponding body facing and garment facing surfaces. The compound sanitary napkin 20 has two centerlines, a longitudinal centerline L and a transverse centerline T. The term "longitudinal", as use herein, refers to a line, axis or direction in the plane of the compound sanitary napkin that is generally aligned with (e.g., approximately parallel to) a vertical plane which bisects a standing wearer into left and right body halves when the compound sanitary napkin is worn. The terms "transverse" or "lateral", as used herein, are interchangeable, and refer, to a line, axis, or direction which lies within the plane of the compound sanitary napkin that is generally perpendicular to the longitudinal direction.

The acquisition/storage member 30 has side edges 24 and end edges 25 which together form the periphery 26 of the acquisition/storage member 30. The accumulation member 50 has side edges 21 and end edges 22 which together form the periphery 23 of the accumulation member and the compound sanitary napkin 20. The bearing member 70 has side edges 71 and end edges 72. The compound sanitary napkin 20 has a first end region 27, a central region 28, and a second end region 29.

The Acquisition/Storage Member

The acquisition/storage member 30 is that component of the compound sanitary napkin 20 intended to first absorb those bodily fluids discharged by a wearer. In the preferred embodiment shown in FIGS. 1–3, the acquisition/storage member stores a portion of such fluids and distributes the remainder to the bearing member 70 for distribution to the accumulation member 50 or directly to the accumulation member 50 for storage therein. The acquisition/storage member 30 comprises an absorbent means 33, such as absorbent element 34, and an outer cover 32 superimposed on the absorbent element 34. (As used herein, the term "superimposed" means adjacent or juxtaposed, but not necessarily in contact with or directly connected with.) Preferably, the entire outer cover 32 is liquid pervious, however, other embodiments are contemplated wherein portions of the outer cover are liquid impervious or hydrophobic.

Further, it has been found that the general shape of the acquisition/storage member 30 can affect the absorbent characteristics of the sanitary napkin 20 as well as the overall comfort to the wearer. In its simplest embodiment (not shown), the acquisition/storage member 30 has a planar configuration similar to a pantiliner which rides on the bearing member 70. For example, a simple execution of the acquisition/storage member 30 of the present invention can comprise an outer cover 32 and an absorbent element 34 that are joined along their longitudinal edges, each having a planar configuration with the bearing member 70 disposed therebetween. Preferably, however, the compound sanitary napkin 20 comprises an acquisition/storage member 30 having a base 10 that is wider than the apex 15 (i.e. that portion of the acquisition/storage member 30 which preferably fits, at least partially, a wearer's interlabial space). The Applicants have found that such a configuration has increased effectiveness and comfort. In other words, the acquisition/storage member 30 preferably has a rounded triangular cross-section as is shown in FIG. 3. Such a rounded triangular cross section may be provided by folding the absorbent element 34 so that the portions thereof that lie laterally outboard of the longitudinal centerline L comprises two plies. such a structure causes the "walls" of the absorbent element 34 to be stiffer than the portions that lie adjacent the longitudinal centerline L. As is discussed below, the increased stiffness provides resiliency to the acquisition/storage member 30. The differential stiffness between the one and two ply portions also provides a preferential fold line for forming the apex 15. Such a folding pattern is also shown in FIG. 3 and is discussed in greater detail below.

As shown in FIG. 3, the acquisition/storage member 30 has a vertical centerline 200, a base 10 having a width B and an apex 15 vertically opposed to the base 10, the apex having a width A. As used herein, the term "base" refers to that portion of the acquisition/storage member 30 having the greatest width B which is adjacent the body facing surface 87 of the accumulation member 50. (The "width" at any given location is determined by measuring the lateral or transverse dimension at that location. Thus, a measurement is taken generally perpendicular to the vertical centerline 200 and generally parallel to the transverse centerline T.) The base 10 is not limited to any particular shape or width, so long as the base 10 has a width B which is greater than the apex 15 width A.

The apex 15 is that portion of the acquisition/storage member 30 which is vertically opposed to the base 10 and the accumulation member 50. The apex 15 may be any shape and may have any width A less than the width B of the base 10. Preferably, the apex 15 is shaped and sized to comfortably reside at least partially within a wearer's interlabial space. Thus, as shown in FIG. 3, the apex 15 is preferably at least partially curved, rounded or otherwise shaped to conform to the wearer's body. Other embodiments, however, are contemplated wherein the apex 15 is flat, pointed or generally non-curvilinear.

The length 40 and the width 41 of the acquisition/storage member 30 can be of any convenient dimension. Preferably, the length of the acquisition/storage member 30 is defined by the length of the central region 28. Such a length provides for easy trifolding of the compound sanitary napkin 20 for packaging. The acquisition/storage member 30, is preferably from about 2 to about 10 cm long, more preferably from about 6 to about 9 cm long, and most preferably from about 7.5 to about 8.5 cm long. A particularly preferred acquisition/storage member 30 has a length of about 8 cm. The width 41 of the preferred embodiment of the acquisition/storage member 30 shown in FIGS. 1–3 contributes to wearing comfort of the compound sanitary napkin 20 of the present invention since at least a portion of the acquisition/storage member 30 is preferably worn interlabially. The acquisition/storage member 30 is preferably from about 0.5 to about 5 cm wide at the base B, more preferably from about 0.5 to about 4 cm wide, and most preferably from about 0.5 to about 3 cm wide.

Outer Cover of the Acquisition/Storage Member

Preferably, the outer cover 32 is compliant, soft feeling, and non-irritating to the wearer's skin. Further, as stated above, at least a portion of the outer cover 32 is liquid pervious, permitting liquid to readily penetrate through its thickness. A suitable outer cover 32 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers.

The outer cover 32 may be a unitary member or may be comprised of two or more elements joined together to form the outer cover 32. Further, any portion of the materials comprising the outer cover 32 may be coated, laminated, treated or otherwise manipulated to impart or enhance any desired characteristics such as strength, flexibility, liquid perviousness or imperviousness.

A preferred outer cover 32 comprises formed film having apertures. Apertured formed films are preferred for the outer cover 32 because they are generally pervious to body exudates and yet non-absorbent, thus reducing the likelihood of liquids passing back through the film and rewetting the wearer's skin. Accordingly, the surface of the formed film which is in contact with the body remains dry, thereby reducing body soiling and creating a more comfortable feel for the wearer. Further formed films are easily manufactured with non-apertured portions that provide liquid impervious areas that prevent any fluids from passing therethrough. Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel, et al. on Aug. 3, 1982; U.S. Pat. No. 4,463,045, issued to Ahr, et al. on Jul. 31, 1984; and U.S. Pat. No. 5,006,394, issued to Baird on Apr. 9, 1991. Each of these patents are incorporated herein by reference. One especially preferred outer cover 32 for the acquisition/storage member 30 of the present invention comprises a formed film described in one or more of the above patents and marketed on sanitary napkins by The Procter & Gamble Company of Cincinnati, OH as "DRI-WEAVE".

In a preferred embodiment of the present invention, the body facing surface of at least a portion of the outer cover 32 is hydrophilic so as to help liquid to transfer through the outer cover 32 faster than if the body facing surface was not hydrophilic. This diminishes the likelihood that menstrual fluid will flow off the outer cover 32 rather than flowing into and being absorbed by the absorbent element 34. In a preferred embodiment, surfactant is incorporated into the polymeric materials of the formed film such as is described in U.S. patent application Ser. No. 08/492,352, entitled "Absorbent Article Having a Nonwoven and Apertured Film Coversheet" filed on Jun. 19, 1995, to be published as a Statutory Invention Registration (number not assigned), the disclosure of which is incorporated herein by reference. Alternatively, the body facing surface of the outer cover 32 can be made hydrophilic by treating it with a surfactant such as described in U.S. Pat. No. 4,950,264 issued to Osborn on Aug. 21, 1990 and which is incorporated herein by reference.

As stated above, the outer cover 32 is preferably superimposed on the absorbent element 34. To insure proper fluid transfer between the outer cover 32 and the absorbent element 34 it is preferred that the outer cover be substantially continuously joined to the underlying absorbent element 34 throughout their common association or interface. By substantially continuously joining the outer cover 32 to the underlying absorbent element 34 the outer cover 32 will have a reduced tendency to separate from the absorbent element 34 during use. Separation of the absorbent core from the outer cover 32 may inhibit fluid transfer from the outer cover 32 into the underlying absorbent element 34. The outer cover 32 may be joined to the absorbent element 34 by any suitable means, including, but not limited to joining the outer cover 32 with the absorbent element 34 with adhesives such as by spray-gluing or applying lines or spots of adhesives between the outer cover 32 and the absorbent element 34. Alternatively, or additionally, the outer cover 32 may be joined with the absorbent element 34 simply by wrapping the outer cover 32 about the absorbent element 34, by entangling the fibers of the absorbent element 34 with the outer cover 32, by fusing the outer cover 32 to the absorbent element 34 with a plurality of discrete individual fusion bonds, or by any other means known in the art. Preferably, the outer cover 32 is joined to the absorbent element 34 by heat, pressure or a combination of heat and pressure commonly known as fusion bonding or dynamic mechanical bonding. Such bonding is described in greater detail in commonly assigned U.S. Pat. No. 5,591,149, issued in the names of Cree, et al. on Jan. 7, 1997, the disclosure of which is incorporated herein by reference.

Referring now to FIG. 3, it can be seen that outer cover 32 completely wraps the absorbent element 34 of the acquisition/storage member 30. The outer cover 32 is shown in FIG. 3 to have a seam 85 adjacent the accumulation member 50. Although such a configuration is advantageous to keep the seam 85 away from any body contact, the figure is not meant to limit the scope of the invention. Other suitable embodiments are contemplated wherein the seam 85 is disposed in any location about the absorbent core. Further, any number of seams, folds, pleats or bonds in the outer cover 32 are acceptable so long as the acquisition/storage member 30 is able to function to absorb bodily fluids as they are exuded while being comfortable to wear.

Figure 4:
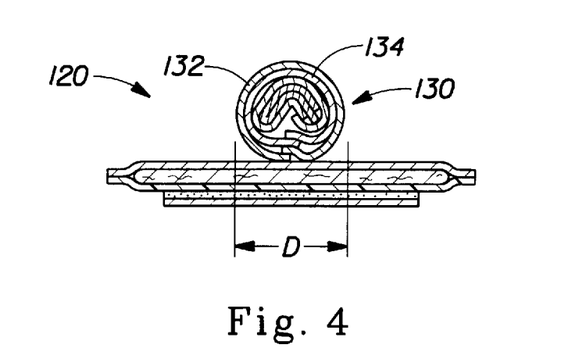
FIG. 4 is a cross-sectional views of an alternative preferred embodiment of the compound sanitary napkin of the present invention.

In another embodiment, compound sanitary napkin 120, as shown in FIG. 4, the outer cover 132 encircles absorbent element 134 to provide alternative acquisition/storage member 130 with a roughly circular cross section having a diameter D. In preferred embodiments of this alternative embodiment of the present invention the acquisition/storage member 130 has a diameter D of between about 1.5 cm and about 5 cm. The Applicants have found that an acquisition/storage member 130 having a roughly circular cross section is relatively insensitive to rotational displacement of the acquisition/storage member that may happen as a wearer positions the compound sanitary napkin for use.

Absorbent Element of the Acquisition/Storage Member

The absorbent element 34 of the present invention primarily functions to absorb bodily fluids as they are exuded, store a portion of such fluids and distribute the remainder of such fluids for storage in the accumulation member 50. Further, in some preferred embodiments, the absorbent element 34 also functions as a shaping member to maintain the shape of the acquisition/storage member 30. Thus, the absorbent element 34 may be any absorbent means which is generally compressible, conformable, resilient, non-irritating to the wearer's skin and capable of absorbing, containing, and transferring body exudates. The absorbent element 34 should have an absorbent capacity of at least about 5 grams of bodily fluids. Preferably, the absorbent element 34 has an absorbent capacity of at least about 10 grams. The absorbent capacity of the absorbent element 34 (i. e., of the acquisition/storage member 30) comprises only a portion of the total absorbent capacity of the compound sanitary napkin 20. The remainder of the absorbent capacity of the compound sanitary napkin 20 being provided by the accumulation member 50 (discussed below).

Further, the absorbent capacity of the compound sanitary napkin 20 may be varied to accommodate wearers ranging in the expected amount of exudate fluid volume by varying either the absorbent capacity of the acquisition/storage member 30 or the accumulation member 50. Since the capacity of the compound sanitary napkin is divided into two portions, one of skill in the art will recognize the flexibility the present invention gives to the designer to provide sanitary napkins meeting wearer needs for both absorbency and comfort. For instance, a different absorbent capacity may be utilized for compound sanitary napkins intended for day time use as compared with those intended for night time use, or for compound sanitary napkins intended for use by teenage females (e. g., a smaller interlabial space can be accommodated by a smaller acquisition/storage member 30) as compared with those intended for more mature women (e. g., a larger pudendal area can be accommodated by a larger accumulation member 50). Alternatively, the relative absorbent capacities may be determined by portion of a wearer's menstrual cycle. For example, in a sanitary napkin 20 designed for the heavy flow portion of a wearer's menstrual cycle, between about 50% and about 75% of the absorbent capacity of the sanitary napkin 20 may be provided by the accumulation member 50. Conversely, in a sanitary napkin designed for the light flow portion of a wearer's menstrual cycle, the acquisition/storage member 30 could provide between about 50% and about 100% of the absorbent capacity of the sanitary napkin 20.

The absorbent element 34 may be manufactured from a wide variety of liquid absorbent materials commonly used in disposable sanitary napkins, and other disposable absorbent articles. Examples of suitable absorbent materials include comminuted wood pulp, which is generally referred to as airfelt; creped cellulose wadding, modified cross-linked cellulose fibers such as those described in U.S. Pat. No. 5,217,445 issued to Young, et al. on Jun. 8, 1993; capillary channel fibers (fibers having intra-fiber capillary channels such as those described in U.S. Pat. No. 5,200,248 issued to Thompson, et al. on Apr. 6, 1993); absorbent foams (e. g., high internal phase emulsion or HIPE foams such as those described in U.S. Pat. No. 5,260,345, issued to DesMarais, et al. on Nov. 9, 1993; U.S. Pat. No. 5,268,244 issued to DesMarais, et al. on Dec. 7, 1993; U.S. Pat. No. 5,331,015 issued to DesMarais et al., on Jul. 19, 1994; and U.S. Pat. No. 5,387,207 issued to Dyer et al., on Feb. 7, 1995 or polyurethane foams as are available from Foamex of Eddystone, Pa. under the trade designation Foamex 08-8982); additional cores comprising foams are described in European Application 0 293 208 BI; sponges (described in U.S. Pat. Nos. 3,512,530; and 3,954,493 and French Patent 2,203,827); thermally bonded airlaid materials such as those material described in U.S. Pat. No. 5,607,414 issued on Mar. 4, 1997 in the name of Richards, et al.; polyurethane, absorbent sponges; synthetic staple fibers; polymeric fibers; hydrogel-forming polymer gelling agents; peat moss; glass fibers or any equivalent materials or combinations of materials. Examples of alternative suitable absorbent cores are described in detail in the above referenced U. S. Statutory Invention Registration H1614 published in the name of Mayer, et al. on Nov. 5, 1996. The disclosure of each of the above identified references is hereby incorporated by reference herein.

Materials selected for use as the absorbent element 34 are preferably compliant, soft, comfortable, compressible and resilient to enhance body fit and comfort of the acquisition/storage member 30. Preferably, the absorbent element 34 is compressible such that the acquisition/storage member 30 will deform under relatively small forces that are experienced during normal use. In addition to being compressible, the materials comprising the absorbent core are preferably conformable such that the acquisition/storage member 30 is able to provide improved fit into and around the labia and perineum. While being generally compressible and conformable under relatively small forces, those forces exerted by the external female genitalia during use, it is also important that the acquisition/storage member 30 be sufficiently resilient such that when it is subjected to normal wearing forces it does not permanently collapse.

In the preferred embodiment shown in FIGS. 1–3, the absorbent element 34 provides the acquisition/storage member 30 with the desired resilient characteristics. Specifically, the material comprising the absorbent element 34 is folded such that there are two plies of material laterally outboard of the longitudinal centerline L. This folding pattern is shown most clearly in FIG. 3. As is also shown in FIG. 3, there is a small gap between the two plies of material immediately adjacent both sides of the longitudinal centerline L. As a result, there is a difference in stiffness between the portion of the absorbent element 34 that is adjacent the longitudinal centerline L and those portions laterally outboard of the longitudinal centerline L. This difference in stiffness results in a preferential fold line along the longitudinal centerline L and enables the preferred rounded triangular cross section of the acquisition/storage member 30. The relatively stiffer two ply portion of the absorbent element 34 also provides resiliency which serves to prevent collapse of the acquisition/storage member 30 when it is exposed to normal wearing forces. While the resilient characteristics of the absorbent element 34 allow for improved fit, they must be balanced against the need for the product to be both soft and comfortable for the wearer.

An especially preferred absorbent element 34 comprises a thermally bonded air laid material, as described above, and in the above referenced U.S. Pat. 5,607,414. As discussed above and shown most clearly in FIG. 3, this material is preferably folded about itself so as to form two layers. Such a folding pattern not only provides resiliency to the absorbent element 34 but also provides absorbent capacity thereto that is less noticeable to a wearer. Specifically, such a folding pattern allows for distribution of bodily fluids along the length of the acquisition/storage member 30 (due to longitudinal flow along the absorbent element 34) while, at the same time, containing at least a portion of such fluid in the interior of the acquisition/storage member (due to lateral flow to the lower ply) where it is less noticeable to a wearer.

As shown in FIG. 3, preferred embodiments of the present invention comprise absorbent cores 34 having a generally triangular cross-section. In this embodiment, the absorbent element 34 is preferably resilient so as to help maintain the desired shape of the acquisition/storage member 30. The absorbent element 34 is preferably elongate, having a dimension in the direction of the length of the sanitary napkin 20. This core configuration provides the acquisition/storage member 30 with a base 10 having a width B wider than the width A of the apex 15. However, the absorbent element 34 may comprise a wide variety of shapes such as rectangular, oval, trapezoidal, pentagonal, U-shaped, Z-folded, and still provide the acquisition/storage member 30 with a base width B greater than apex width A. An example of an alternative embodiment having a circular cross-section for the absorbent element is shown in FIG. 4 as 134.

Alternative Embodiments of the Acquisition/Storage Member

In an alternative embodiment (not shown) the absorbent element 34 may be wrapped in an acquisition layer that is disposed between the absorbent element 34 and the outer cover 32. The acquisition layer may serve several functions including improving wicking of exudates. By improving the wicking of exudates, the acquisition layer provides a more even distribution of the exudates throughout the absorbent element 34 and facilitates transfer of such exudates to the accumulation member 50. The acquisition layer may comprise any of the materials as further described hereinbelow with regard to acquisition layers. A particularly preferred acquisition layer comprises a nonwoven web, such as the nonwoven web available from Fiberweb Corporation of Simpsonville, SC under the trade designation P-9. In a preferred embodiment, the acquisition layer may be joined with the outer cover 32 by any of the conventional means for joining webs together, most preferably by fusion bonds as is more fully described in the above mentioned U.S. Pat. No. 5,591,149.

In alternative preferred embodiments, a separate resilient member (not shown) can be provided. The resilient member may extend throughout the entire length of the acquisition/storage member 30. Alternatively, the resilient member may only extend through a portion of the length of the acquisition/storage member 30. The resiliency of the resilient member is preferably not affected by the presence of body exudates absorbed by and contained within the absorbent core. The sustained resiliency of the resilient member permits the acquisition/storage member 30 to maintain intimate contact with the body of the wearer during use. As further discussed below, a resilient member can provide the acquisition/storage member 30 with the desired resilient characteristics such that the acquisition/storage member 30 conforms to the contours of the body to provide intimate contact with the exposed genitalia of the female wearer. Intimate contact with the exposed female genitalia helps provide better fluid transfer from the wearer into the acquisition/storage member 30 without allowing fluid to bypass and/or run off the acquisition/storage member 30.

For example, referring to FIG. 3, a resilient member could be provided between the absorbent element 34 and the bearing member 70 to lift the absorbent element 34 above the bearing member 70 for improved body contact. The acquisition/storage member 30 may comprise a single resilient member or a plurality of resilient members. The resilient member may be absorbent, however it need not be so. Suitable materials which may be used as the resilient member include, but are not limited to nylon, polypropylene, polyurethane, polyethylene, polyester, synthetic rubber, glass fibers and other synthetic materials such as formed films, or natural materials such as rubber, sponges, and the like or any suitable material which is capable of resisting collapse under normal wearing conditions of sanitary napkins during use. One preferred resilient member comprises polyurethane foam available from Foamex under the trade designation Foamex 08-8982. The resilient member may be manufactured in a wide variety of shapes such as rectangular, triangular, oval, square, pentagonal, U-shaped, Z-folded or any other shape as is known in the art. Other suitable resilient members are described in U.S. Pat. No. 5,558,656, issued in the name of Carl L. Bergman on Sep. 24, 1996, and in U.S. Pat. No. 5,591,148, issued in the name of Mc Fall, et al., on Jan. 7. 1997. The disclosure of each of these patents is incorporated herein by reference.

Accumulation Member

The second component of the compound sanitary napkin 20 of the present invention is the accumulation member 50. The accumulation member receives and stores bodily fluids that have been absorbed by the acquisition/storage member 30, distributed therethrough and through the bearing member 70. Because, as is discussed below with respect to the bearing member 70, the bodily fluids have already been distributed along a substantial portion of the longitudinal length of the compound sanitary napkin 20 by the acquisition/storage member 30 and the bearing member 70, the storage capacity of the accumulation member 50 is very efficiently used. As a result, the accumulation member can be relatively thin and flexible while, at the same time, storing a meaningful quantity of bodily fluids.

The accumulation member can be of generally rectangular shape, as is shown in FIG. 1. However, other suitable shapes include but are not limited to oval, hourglass (FIG. 5), dog-bone, asymmetric and other shapes that are known in the art.

As shown in FIG. 1, the accumulation member 50 preferably has a length 60 and a width 61. The accumulation member 50 is preferably from about 20 to 40 cm long, more preferably from about 20 to 35 cm long, and most preferably is about 25 cm long. The accumulation member 50 is preferably from about 5 to 20 cm in width, more preferably from about 5 to 15 cm in width, and most preferably from about 7 to 12 cm in width. Preferably, the width of the accumulation member 50 is at least 1.5 times the width B of the base of the acquisition/storage member 30. More preferably, the width of the accumulation member 50 is at least 2 times the width B of the base of the acquisition/storage member 30. Most preferably, the width of the accumulation member 50 is in the range from about 3 to about 8 times the width B of the base of the acquisition/storage member 30. The accumulation member 50 preferably has a caliper of less than about 20 millimeters, more preferably less than about 15 millimeters, even more preferably less than about 7 millimeters, and most preferably less than about 3 millimeters.

As is shown most clearly in FIG. 3, the accumulation member 50 preferably comprises a liquid impervious backsheet 54, a liquid pervious topsheet 52 joined with the backsheet 54 and an absorbent core 56 positioned between the topsheet 52 and the backsheet 54. As shown in FIG. 3, the topsheet 52 may form at least a portion of the body contacting surface 87 of the accumulation member 50 and the backsheet 54 may form at least a portion of the garment surface 55.

Topsheet of the Accumulation Member

The topsheet 52 can be any fluid pervious material commonly used in sanitary napkins, disposable diapers, and the like. The topsheet 52 can be any of the materials described above as being useful in the outer cover 32 of the acquisition/storage member 30, including, but not limited to nonwovens and apertured formed films. Preferably, the topsheet 52 comprises the same formed film material discussed above with respect to the outer cover 32 which is marketed on sanitary napkins by The Procter & Gamble Company of Cincinnati, Ohio as "DRI-WEAVE".

In alternative preferred embodiments, the accumulation member 50 may also comprise a wipe acquisition layer or secondary topsheet as described in U.S. Pat. No. 4,950,264 issued to Osborn on Aug. 21, 1990 the disclosure of which is incorporated herein by reference. Such a layer serves to provide improved masking of the bodily fluids that are absorbed by the absorbent core 42 and would be positioned between the topsheet 52 and the absorbent core 56. The secondary topsheet layer of the accumulation member 50 may comprise any of the materials described above with regard to the acquisition/storage member's 30 acquisition layer as is discussed above. A suitable material for such a layer is the hydrophilic, thermally bonded, carded polypropylene nonwoven material having a staple denier of less than 2.5 dpf and a basis weight of about 23 grams per square meter (gsm) which is available from the Veratec Division of International Paper, Lewisburg, Pa.

The Absorbent Core of the Accumulation Member

The absorbent core 56 of the accumulation member 50 primarily functions to protect the wearer's garments from soiling by absorbed fluids which are transferred from the acquisition/storage member 30 or which may inadvertently bypass the acquisition/storage member 30.

The absorbent core 56 may comprise any of the materials described above as being useful in the absorbent element 34. The absorbent core 56 may be manufactured from a wide variety of liquid absorbent materials commonly used in disposable sanitary napkins, diapers, and other absorbent articles. Examples of suitable absorbent materials include comminuted wood pulp which is generally referred to as airfelt, creped cellulose wadding, absorbent foams, absorbent sponges, synthetic staple fibers, polymeric fibers, hydrogel-forming polymer gelling agents, or any equivalent materials or combinations of materials. Particularly preferred absorbent materials are polymeric gelling agents or superabsorbent polymers. Polymeric gelling agents are those materials which, upon contact with fluids, such as water or body fluids, imbibe such fluids and thereby form hydrogels. In this manner, fluid discharged into the absorbent core 56 can be acquired and held by the polymeric gelling agent, thereby providing the articles herein with enhanced absorbent capacity and/or improved fluid retention performance.

In the preferred embodiment shown in FIGS. 1 to 3, the absorbent core 56 is a laminate comprised of a layer of superabsorbent polymer material disposed between two plies of air-laid tissue. Such a structure is described more completely in the above mentioned U.S. Pat. No. 4,950,264. Alternatively, particularly when a relatively thick absorbent core 56 is desired, the absorbent core 56 can comprise an air laid fibrous assembly, with or without, a superabsorbent polymer, as is known to the art.

Backsheet of the Accumulation Member

The backsheet 54 of the accumulation member 50 is preferably impervious to liquids (e.g., menses and/or urine) and is preferably manufactured from a thin, flexible plastic film, although other flexible liquid impervious materials may also be used. As used herein, the term "flexible" refers to materials which are compliant and will readily conform to the general shape and contours of the human body. In use, the backsheet 54 is interposed between the absorbent core 56 and the wearer's undergarments. The function of the backsheet 54 is to prevent exudates which may be expelled from the absorbent core 56 from contacting and soiling the wearer's undergarments. The backsheet 54 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.015 mm (2.0 mil). Exemplary polyethylene films are manufactured by Clopay Corporation of Cincinnati, Ohio under the designation P1 8-0401 and by Ethyl Corporation, Visqueen Division, of Terre Haute, Ind., under the designation XP-39385. The backsheet is preferably embossed and/or matte finished to provide a more clothlike appearance. Further, the backsheet may permit vapors to escape from the absorbent core 56 (i.e., breathable) while still preventing exudates from passing through the backsheet.

Attachment Means of the Accumulation Member

In preferred embodiments, the accumulation member 50 is provided with a support means or attachment means, such as adhesive attachment means 58. The adhesive attachment means 58 provides a means for securing the compound sanitary napkin 20 in the crotch portion of the wearer's undergarment or panty. Thus, a portion or all of the outer or garment surface 55 of the backsheet 54 is coated with adhesive. In a preferred embodiment, at least a portion of the adhesive 58 is positioned on the garment surface 55 of the backsheet 54 adjacent the longitudinal side edges 21 of the accumulation member 50. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697.

The pressure-sensitive adhesive is typically covered with a removable release liner 59 in order to keep the adhesive from drying out or adhering to a surface other than the crotch portion of the panty prior to use. Suitable release liners are also described in the above referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The compound sanitary napkin 20 of the present invention is used by removing the release liner 59 and thereafter placing the sanitary napkin in a panty so that the adhesive 58 contacts the panty. The adhesive 58 maintains the sanitary napkin in its position within the panty during use.

Assembly of the Accumulation Member

As noted above, the absorbent core 56 is positioned between the topsheet 52 and the backsheet 54. Preferably, as shown in FIG. 3, the topsheet 52 and the backsheet 54 have length and width dimensions generally larger than the absorbent core 56 so that they extend beyond the edges of the absorbent core 56 where they are associated together in a suitable manner. As used herein, the term "associated" encompasses configurations whereby a first member is directly joined to a second member and configurations whereby a first member is indirectly joined to a second member by affixing the first member to intermediate members which in turn are affixed to the second member. The extension of the topsheet 52 and/or the backsheet 54 beyond the end edges and the side edges of the absorbent core 56 form the end edges 22 and the side edges 21, respectively, of the accumulation member 50. In a preferred embodiment, the backsheet 54 and the topsheet 52 have the rounded rectangular shape shown in FIG. 1 and extend beyond the absorbent core 56 a distance of at least about 1.0 centimeter where they are joined directly to each other by attachment means as are well known in the art. The attachment means may be, for example, a uniform continuous layer of adhesive a patterned layer of adhesive, an array of separate lines or spots of adhesives, heat bonds, pressure bonds, ultrasonic bonds, dynamic mechanical bonds, or any other suitable attachment means or combinations of these attachment means as are known in the art. Preferably, the attachment means comprises dynamic mechanical bonds as described in the above mentioned U.S. Patent 5,591,149.

Alternative Embodiments of the Accumulation Member

The accumulation member 50 may also have flaps (not shown) which extend laterally from the side edge 21 of the accumulation member 50. A number of sanitary napkins having flaps suitable or adaptable for use with the accumulation member 50 of the compound sanitary napkin 20 of the present invention are disclosed in U.S. Pat. No. 4,687,478 issued to Van Tilburg on Aug. 18, 1987; U.S. Pat. No. 4,589,876 issued to Van Tilburg on May 20, 1986; and U.S. Pat No. 4,608,047 issued to Mattingly on Aug. 26, 1986. Each of these patents are incorporated herein by reference.

Optionally, the accumulation member may comprise components that naturally wrap the sides of a wearer's panties. A sanitary napkin having components that naturally wrap the sides of a wearer's panties suitable for use with the accumulation member of the compound sanitary napkin 20 of the present invention are disclosed in U.S. Pat. No. 5,584,829, issued Dec. 17, 1996, in the names of Lavash, et al. and U.S. Pat. No. 5,558,663, issued Sep. 24, 1996, in the names of Weinberger, et al. The disclosures of the preceding patents are incorporated herein by reference.

The individual components of the acquisition/storage member 30 and the accumulation member 50 may be comprised of components that are extensible (preferably, capable of stretching) particularly in the longitudinal direction when the compound sanitary napkin is worn. Preferably, a stretchable compound sanitary napkin is capable of elongating in the longitudinal direction between about 15% and about 40% of its unstretched length. This extensibility provide better in-use fit, comfort, and decreased staining when the compound sanitary napkin is affixed to the wearer's undergarments. Sanitary napkins having extensible components are described in U.S. Pat. No. 5,611,790 issued in the name of Osborn, et al. on March 18, 1997 and in U.S. patent application Ser. No. 07/915,284 filed July 23, 1992, in the name of Osborn, et al. (PCT Publication No 93/01786, published Feb. 4, 1993). The disclosures of the preceding patents and publications are incorporated herein by reference. An example of a component combing the benefits of a pressure sensitive adhesive and a backsheet is an extended adhesive film known as Formula #198–388 manufactured by the Findley Adhesives Company of Wauwatosa, Wis.

The Bearing Member

As is also shown in FIGS. 1–3, bearing member 70 connects the acquisition/storage member 30 and the accumulation member 50. As is shown most clearly in FIGS. 1 and 2, the acquisition/storage member 30 is slidably attached to the bearing member 70 and the bearing member 70 is joined to the accumulation member 50 adjacent their respective end edges 72, 22. The slidable attachment of the acquisition/storage member 30 and the bearing member 70 allows a wearer to position the acquisition/storage member for maximum effectiveness in intercepting bodily fluids as they are exuded from her body. That is the compound sanitary napkin 20 of the present invention can be adjusted to correspond to an individual wearer's anatomy and life style. For example, for night time wear, when wearer's often experience rear leakage (i. e., along the gluteal groove) from sanitary napkins of the current art, a wearer could position the acquisition/storage member 30 forward along the bearing member 70 so that more of the accumulation member 50 can be disposed in her gluteal groove to lessen the risk of such rear leakage.

In its simplest execution (not shown), the bearing member 70 comprises any means suitable for slidably connecting the acquisition/storage member 30 and the accumulation member 50. For example, a simple execution of the bearing member 70 could comprise a pair of longitudinally spaced apart strings that are joined to the accumulation member 50 adjacent the longitudinal ends 22 thereof. Preferably, however, for the preferred embodiment of the present invention that is shown in FIGS. 1–3, the bearing member 70 comprises a connecting member 74 and a distribution member 76. The connecting member 74 is the primary connecting element between the acquisition/storage member 30 and the accumulation member 50. That is, the acquisition/storage member 30 can longitudinally slide on the connecting member 74 allowing a wearer to position it relative to the accumulation member as she desires. The connecting member 74 is also at least porous to bodily fluids allowing them to transfer from the acquisition/storage member 30 to the distribution member 76 or the accumulation member 50. The distribution member 76 serves to longitudinally distribute absorbed bodily fluids as they are being transferred from the acquisition/storage member 30 to the accumulation member 50.

The Connecting Member

As can be seen most clearly in FIGS. 1 and 2, the connecting member 74 is symmetrically disposed about the longitudinal centerline L and extends substantially the entire longitudinal length of the compound sanitary napkin 20. The connecting member 74 is also joined to the accumulation member 50 adjacent their respective end edges 72, 22 using means known to those of skill in the art. For example, the connecting member 70 may be joined to the accumulation member 50 by heat bonds, pressure bonds, ultrasonic bonds, dynamic mechanical bonds, or any other suitable attachment means or combinations of these attachment means as are known in the art. Preferably, the attachment means comprises dynamic mechanical (fusion) bonds as described in the above mentioned U.S. Pat. No. 5,591,149.

Because the acquisition/storage member 30 is intended to slide on the connecting member 74, the connecting member should have a relatively low coefficient of friction. Also, the connecting member 74 should not have any snags or protuberances that would interfere with adjusting the longitudinal position of the acquisition/storage member 30. For example, the connecting member 74 should not comprise a material having fibers that could intertwine with any fibers in the acquisition/storage member 30 so it would be difficult to slide the acquisition/storage member 30. As also noted above, at least a portion of the connecting member 74 should be porous to bodily fluids to facilitate transfer of such fluids from the acquisition/storage member 30 to the accumulation member 50.

Preferably, the connecting member 74 is compliant, soft feeling, and nonirritating to the wearer's skin. Further, as stated above, at least a portion of the connecting member 74 is liquid pervious, permitting liquid to readily penetrate through its thickness. A suitable connecting member 74 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. One especially preferred material for the connecting member 74 is a formed film described above with respect to the outer cover 32 of the acquisition/storage member 30 and marketed on sanitary napkins by The Procter & Gamble Company of Cincinnati, Ohio as "DRI-WEAVE".

The Distribution Member

The distribution member 76 extends only a portion of the longitudinal length of the compound sanitary napkin 20. Preferably, the distribution member 76 is symmetrically disposed about the longitudinal centerline L and the transverse centerline T and extends at least the longitudinal length of the central region 28. More preferably, the distribution member 76 extends partially into the first and second end regions 27, 29 to further distribute absorbed bodily fluids throughout the available absorption volume of the accumulation member 50.

The distribution member 76 may be joined to the connecting member 74 by any of the conventional means for joining webs together. For example, the distribution member 76 and the connecting member 74 may be secured by a uniform continuous layer of adhesive, a patterned layer of adhesive, or an array of separate lines, spirals, or spots of adhesive. Alternatively, the attachment means may comprise heat bonds, pressure bonds, ultrasonic bonds, dynamic mechanical bonds, or any other suitable attachment means or combinations of these attachment means as are known in the art. Preferably, the attachment means comprises dynamic mechanical bonds as described in the above mentioned U.S. Pat. No. 5,591,149.

A suitable distribution member 76 may be manufactured from a wide range of materials such as woven and nonwoven materials. Suitable woven and nonwoven materials can be comprised of natural fibers (e.g., wood or cotton fibers), synthetic fibers (e.g., polymeric fibers such as polyester, polypropylene, or polyethylene fibers); or from a combination of natural and synthetic fibers. A preferred nonwoven material for use as the distribution member 76 may comprise carded, melt blown, or spun bonded nonwovens wherein the nonwoven material comprises either natural or synthetic fibers. A particularly preferred nonwoven material for the distribution member 76 comprises a hydrophilic, spun bonded material having a basis weight of about 0.68 ounces per square yard (23 grams per square meter) such as is supplied by Corovin GmbH of Penne, Germany as Corolind H23GSM.

Alternatively, the distribution member 76 can comprise a wet laid tissue as may be known to the art. A suitable tissue has a basis weight of about 12 pounds per 3000 square feet (19.5 grams per square meter) and is available from Georgia-Pacific Corp. of Bellingham, Wash. under the designation DST-1.

Alternative Embodiment of the Bearing Member

Figure 5:
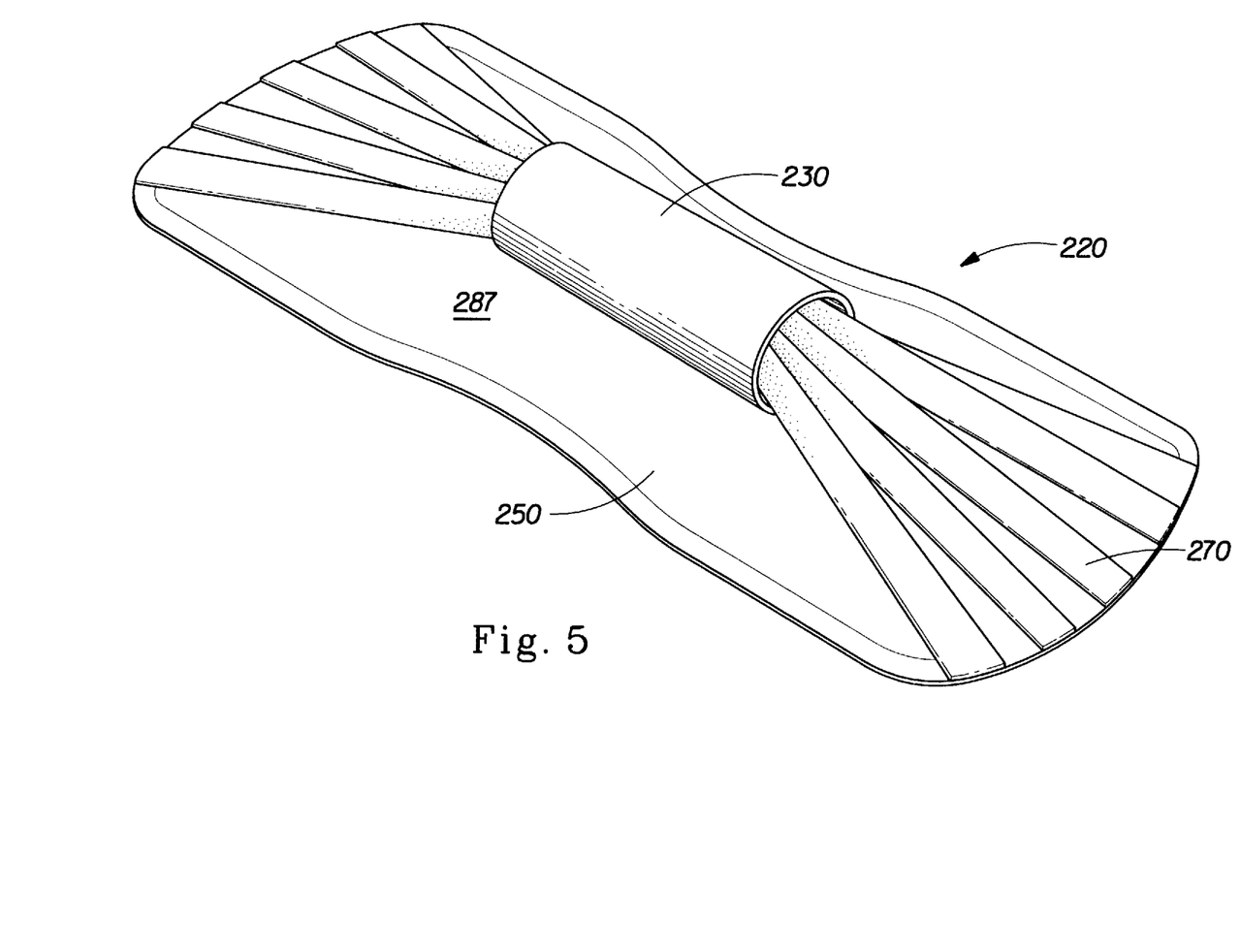
FIG. 5 is a perspective view of a second alternative preferred embodiment of the compound sanitary napkin of the present invention.

In an alternative embodiment of the present invention, compound sanitary napkin 220, the bearing member, shown as 270 in FIG. 5, the bearing member has a greater transverse width than the acquisition/storage member 230. As can also be seen in FIG. 5, the bearing member 270 is constricted as it passes through acquisition/storage member 230. As a result, bodily fluids that are transferred from acquisition/ storage member 230 are spread both longitudinally and laterally as they are distributed by the bearing member 270. This means such fluids are transferred to a greater portion of the body surface 287 of accumulation member 250 and utilization of the absorbent capacity of accumulation member 250 is less dependent on the wicking properties of the materials comprising the accumulation member 250.

While webs comprising cellulosic or other non thermoplastic materials are suitable for use with this alternative embodiment of the bearing member 270, thermoplastic materials are particularly preferred because they can be readily bonded to underlying structure using dynamic mechanical bonding as described in the above mentioned U.S. Pat. No. 5,591,149. One especially preferred material for the alternative bearing member 270 is a formed film described above with respect to the outer cover 32 of the acquisition/storage member 30 and marketed on sanitary napkins by The Procter & Gamble Company of Cincinnati, OH as "DRI-WEAVE".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound sanitary napkin having a longitudinal length and a lateral width and comprising:
    a acquisition/storage member comprising an absorbent element and an outer cover;
    an accumulation member having a pair of opposed end edges and comprising a liquid impervious backsheet and an absorbent core joined to said backsheet; and
    a bearing member overlying said accumulation member, said bearing member having a pair of opposed end edges and connecting said acquisition/storage member to said accumulation member, wherein said acquisition/ storage member is slidably connected to said bearing member and one of said end edges of said bearing member is joined to one of said end edges of said accumulation member and the other of said end edges of said bearing member is joined to the other of said end edges of said accumulation member.

2. The compound sanitary napkin of claim 1 wherein said acquisition/storage member comprises a base having a width and an apex having a width, said base being juxtaposed said accumulation member and said apex being vertically opposed to said base, said base width being greater than said apex width such that said acquisition/storage member has a generally triangular cross-section.

3. The compound sanitary napkin of claim 1 wherein said absorbent element comprises a thermally bonded, air laid material.

4. The compound sanitary napkin of claim 1 wherein said absorbent element comprises a foam.

5. The compound sanitary napkin of claim 4 wherein said absorbent element comprises a HIPE foam.

6. The compound sanitary napkin of claim 1 wherein said acquisition/storage member comprises an acquisition layer.

7. The compound sanitary napkin of claim 1 wherein said acquisition/storage member comprises a resilient member.

8. The compound sanitary napkin of claim 7 wherein said resilient member comprises a foam.

9. The compound sanitary napkin of claim 8 wherein said resilient member comprises a polyurethane foam.

10. The compound sanitary napkin of claim 7 wherein said resilient member is wrapped in an acquisition layer.

11. The compound sanitary napkin of claim 1 wherein said accumulation member has a periphery and further comprises a topsheet disposed on said absorbent core and joined to said backsheet about said periphery.

12. The compound sanitary napkin of claim 1 wherein said bearing member comprises a connecting member and a distribution member.

13. A compound sanitary napkin having a longitudinal length and a lateral width and comprising:
    a acquisition/storage member having a base with a width and an apex with a width, said base being juxtaposed said accumulation member and said apex being vertically opposed to said base, said base width being greater than said apex width such that said acquisition/ storage member has a generally triangular cross-section, said acquisition/storage member comprising an absorbent element and an outer cover;
    an accumulation member having a periphery and a pair of opposed end edges and comprising a liquid impervious backsheet, a liquid pervious topsheet joined to said backsheet about said periphery, and an absorbent core disposed between said backsheet and said topsheet; and
    a bearing member having a pair of opposed end edges connecting said acquisition/storage member to said accumulation member wherein said acquisition/storage member is slidably connected to said bearing member and said end edges of said bearing member are joined to said accumulation member adjacent end edges thereof.

14. The compound sanitary napkin of claim 13 wherein said bearing member comprises a connecting member and a distribution member.

* * * * *